United States Patent [19]

Yamashita et al.

[11] Patent Number: 5,089,276

[45] Date of Patent: Feb. 18, 1992

[54] CALCIUM PANTOTHENATE COMPOSITE

[75] Inventors: Junzou Yamashita, Toyonaka; Yasuo Ono; Kunihiko Sumimura, both of Osaka, all of Japan

[73] Assignee: Takeda Chemical Industries, Ltd., Osaka, Japan

[21] Appl. No.: 510,686

[22] Filed: Apr. 18, 1990

[30] Foreign Application Priority Data

Apr. 19, 1989 [JP] Japan .................. 1-099637
Jul. 11, 1989 [JP] Japan .................. 1-179440

[51] Int. Cl.$^5$ .............. A61K 33/10; A61K 31/19; A61K 31/195
[52] U.S. Cl. .................. 424/686; 424/687; 514/557; 514/563
[58] Field of Search ............ 514/563, 557; 424/686, 424/687

[56] References Cited

U.S. PATENT DOCUMENTS 3,092,548 6/1963 Worton .................. 167/55
3,247,064 4/1966 Maekawa et al. .......... 167/81

FOREIGN PATENT DOCUMENTS 43-20569 9/1968 Japan .
44-9289 4/1969 Japan .

OTHER PUBLICATIONS

Chemical Abstracts 87(6):44247 Georgescu et al. (1977).
Chemical Abstracts 88(2): 11930 Georgescu et al. (1978).
Chemical Abstracts 93(4): 31777 Intreprinderea de Medicamento "Biofarm" (1980).

Primary Examiner—Frederick E. Waddell
Assistant Examiner—Raymond J. Henley, III.
Attorney, Agent, or Firm—Wenderoth, Lind & Ponack

[57] ABSTRACT

A composite which is obtainable by mixing calcium pantothenate with a per se neutral or basic magnesium or calcium lactate or carbonate in the presence of water and/or a lower alcohol, and drying the resulting mixture, is stable with little decrease of the content of calcium pantothenate during storage.

When other drugs, which may cause changes as the result of combination with calcium pantothenate, are combined to produce various preparations, the composite is stable because they are hardly affected by other ingredients and hardly affect other ingredients; for example, in production of tablets, powders, granules, and capsules, complicated processes to separate from other ingredients are not required, and the excessive amount in anticipation of the loss along with time can be reduced markedly.

8 Claims, No Drawings

CALCIUM PANTOTHENATE COMPOSITE

FIELD OF THE INVENTION

The invention relates to a stable granular or powdery composite of calcium pantothenate which can be advantageously used for production of vitamin-containing products such as tablets, pills, capsules, powders, and granules used in the field of food, medicines, and fodders in the livestock industry.

BACKGROUND OF THE INVENTION

Calcium pantothenate is often processed into preparations in the form of tablets, powders, granules, and capsules by combining with other vitamins.

Calcium pantothenate itself is relatively stable but its decomposition is accelerated markedly by combination of other vitamins such as ascorbic acid, thiamine, or pyridoxine. Conversely, calcium pantothenate accelerates the decomposition of vitamins such as ascorbic acid, thiamine, and pyridoxine.

Simple mixing of the ingredients, as in the conventional vitamin complex preparations, will not stabilize calcium pantothenate and the drugs combined together.

For these reasons, various attempts have been made to stabilize calcium pantothenate in the solid preparations such as medicines, food, fodders in the livestock industry, etc.

For example, an excessive amount of the compound is combined in anticipation of loss along with time, so as to make up for the loss due to decomposition.

A method for stabilization of the compound in tablets has been proposed in which the compound is separated from other ingredients by preparing dry-coated tablets or multiple compressed tablets, or by adding calcium pantothenate to the coating layer such as the sugar layer in sugar-coated tablets (U.S. Pat. No. 3,247,064).

Also an attempt is made to delay the decomposition of the ingredients by granulating each ingredient separately so that the ingredients come in contact with each other more scarcely.

However these attempts are not industrially and economically advantageous because the procedures are complicated and uniformity of content should be confirmed during the processes.

Thus it has been desired to obtain stable calcium pantothenate composites wherein the compound is hardly decomposed even in the presence of other drugs.

SUMMARY OF THE INVENTION

The present inventors have found that by a very simple method wherein calcium pantothenate with a per se neutral or basic magnesium or calcium lactate or carbonate are mixed in the presence of water and/or a lower alcohol, the stability of the calcium pantothenate itself can be retained and better compatibility with other drugs can be assured than when calcium pantothenate powders are used, and have completed the invention based on the finding.

DETAILED DESCRIPTION OF THE INVENTION

Namely this invention relates to a composite which is obtainable by mixing calcium pantothenate with a per se neutral or basic magnesium or calcium lactate or carbonate in the presence of water and/or a lower alcohol, and drying the resulting mixture.

The per se neutral or basic magnesium or calcium lactates or carbonates used in this invention are exemplified by calcium lactate, magnesium carbonate, and calcium carbonate. Among these, calcium lactate is preferable.

These substances may be used as far as they are on the market.

Calcium lactate is commercially available as anhydrous and as hydrated, both of which are usable for this invention.

Calcium carbonate used in this invention may be heavy, light, or colloidal.

The amount of the per se neutral or basic magnesium or calcium lactate or carbonate to be combined is unlimited and may be selected appropriately from a broad range, usually accounting for 10 weight % or more, preferably 20 to 90 weight %, more preferably 40 to 75 weight %, of the total amount of the composite.

When a per se neutral or basic magnesium or calcium lactate or carbonate combined accounts for 90 weight % or more, a large amount of the composite should be combined; then when calcium pantothenate is combined with other drugs, the combination balance is sometimes undesirable. On the other hand, when a per se neutral or basic magnesium or calcium lactate or carbonate combined accounts for 10 weight % or less, calcium pantothenate does not disperse uniformly, resulting in undesirable compatibility with other drugs.

Commercially available calcium pantothenate are usable whether they are amorphus or crystals; neither chemical stability nor compatibility is different between amorphous and crystalline preparations.

The lower alcohol has 1 to 4 carbon atoms, for example methyl alcohol, ethyl alcohol, propyl alcohol, isopropyl alcohol, butyl alcohol, isobutyl alcohol, preferably methyl alcohol or ethyl alcohol.

The amount of water and/or a lower alcohol is unlimited and can be selected appropriately from a broad range according to the ratio of calcium pantothenate and the per se neutral or basic magnesium or calcium lactate or carbonate, preferably 4 volume parts or more, more preferably to 20 to 200 volume parts per 100 weight parts of the mixture of calcium pantothenate and a per se neutral or basic magnesium or calcium lactate or carbonate.

The composite of this invention is obtained by mixing calcium pantothenate with per se neutral or basic magnesium or calcium lactate or carbonate in the presence of water and/or a lower alcohol, and drying the resulting mixture.

The composite according to the invention can be produced by mixing, for example, wet granulation such as keading and fluidization granulation, spray drying, and so on.

For example, the composite of this invention can be prepared by the following techniques.

(1) by kneading i) Calcium pantothenate is kneaded with a per se neutral or basic magnesium or calcium lactate or carbonate in the presence of water and/or a lower alcohol. The amount of water and/or a lower alcohol used for kneading and the extent of kneading may be selected appropriately according to the ratio of calcium pantothenate and the per se neutral or basic magnesium or calcium lactate or carbonate. Kneading is performed to the extent that calcium pantothenate has been dissolved in water and/or a lower alcohol completely or partly and loaded onto the per se neutral or basic magnesium or calcium lactate or carbonate.

For example the amount of water and/or a lower alcohol is 4 weight, parts or more, preferably 5 to 25 weight parts, per 100 weight parts of the mixture of the per se neutral or basic magnesium or calcium lactate or carbonate and calcium pantothenate.

The kneaded mixture is dried, and pulverized or granulated, to give the composite.

ii) Calcium pantothenate is dissolved in water and/or a lower alcohol, and the solution is added to a per se neutral or basic magnesium or calcium lactate or carbonate, which is then kneaded. The kneaded mixture is dried, and pulverized or granulated, to give the composite. This procedure is particularly efficient when the content of calcium pantothenate in the composite is less than 40 weight %.

It is desirable that the solution of calcium pantothenate used here is of a concentration close to that of the saturated solution.

(2) by fluid bed spray granulation

A solution of calcium pantothenate in water and/or a lower alcohol is sprayed and allowed to disperse with a per se neutral or basic magnesium or calcium lactate or carbonate being fluidized in a fluid bed granulator.

The solution of calcium pantothenate used here is of a concentration of 5 to 30% (W/W), preferably 10 to 20%.

(3) by spray drying

A solution of calcium pantothenate and a per se neutral or basic magnesium or calcium lactate or carbonate in water and/or a lower alcohol is subjected to spray drying in a stream of about 120° to 180° C. to give a composite.

(4) A solution of calcium pantothenate in water and/or a lower alcohol is added to a solution of a per se neutral or basic magnesium or calcium lactate or carbonate in water and/or a lower alcohol, and the mixture is allowed to stand at room temperature to give a creamy solid.

The thus-obtained creamy solid is dried, and pulverized or granulated to give the composite.

When calcium lactate is used as a per se neutral or basic magnesium or calcium lactate or carbonate in this invention, all or a part of the composite may make eutectic crystals.

The composite thus obtained is different from those obtained by simple mixing of the ingredients. Therefore not only the decomposition of calcium pantothenate itself but also the decomposition of other ingredients by calcium pantothenate is suppressed even when other drugs are combined which may cause interaction.

In addition, by the techniques described above, it is possible to produce the composites of the invention in various solid forms such as powders, fine granules, and granules.

Especially for compressing after combining the composite directly with other drugs, fine granules are desirable.

The composite of this invention may contain additional ingredients such as excipients, stabilizers, and binders.

The composite of this invention is stable with little decrease of the content of calcium pantothenate during storage.

When other drugs, which may cause changes as the result of combination with calcium pantothenate, are combined to produce various preparations, the composite is stable because it is hardly affected by other ingredients are hardly affects other ingredients; for example, in production of tablets, powders, granules, and capsules, complicated processes to separate from other ingredients are not required, and the excessive amount in anticipation of the loss along with time can be reduced markedly.

The composite of this invention is advantageous especially in production of tablets, because complicated processes to make multilayer tablets are unnecessary and the composite can be mixed directly with other ingredients and subjected to tableting.

The following examples and test examples will illustrate the invention more concretely. The materials used in the examples are all powders but the invention should not be limited only to these.

EXAMPLE 1

50 g of calcium pantothenate (Daiichi Seiyaku Co., Ltd ; JP grade) was dissolved by warming in 50 ml of pure water. 50 g of colloidal calcium carbonate (manufactured by Shiraishi Karusium Co.: Colocarso S) was placed in a mortar, to which 36.7 g of the calcium pantothenate solution described above was added, and the mixture was kneaded.

The kneaded mixture was dried at 40° C. under reduced pressure, the dried material was pulverized by a table grinder to give a composite (containing 27 weight % of calcium pantothenate). The composite was white powders.

EXAMPLE 2

50 g of colloidal calcium carbonate (manufactured by Shiraishi Karusium Co.: Colocarso S) and 50 g of calcium pantothenate were mixed in a mortar, to which 10.0 ml of pure water was added, and the mixture was kneaded.

The kneaded mixture was dried at 40° C. under reduced pressure, the dried material was pulverized by a table grinder to give a composite (containing 50 weight % of calcium pantothenate). The composite was white powders.

EXAMPLE 3

500 g of colloidal calcium carbonate (manufactured by Shiraishi Karusium Co.: Colocarso S) and 500 g of calcium pantothenate (Daiichi Seiyaku Co., Ltd.: JP grade) were mixed in a vertical granulator Type FM-VG-10 (manufactured by Fuji Sangyo Co., Ltd.) for 5 minutes, to which 100 ml of pure water was added, and the mixture was kneaded for 10 minutes.

The kneaded mixture was dried at 40° C. under reduced pressure, the dried material was pulverized by an atomizer to give a composite (50 weight %). The composite was white powders.

EXAMPLE 4

500 g of colloidal calcium carbonate (manufactured by Shiraishi Karusium Co.: Colocarso S) and 500 g of crystalline calcium pantothenate (Daiichi Seiyaku Co., Ltd.: JP grade) were mixed in a vertical granulator Type FM-VG-10 (manufactured by Fuji Sangyo Co., Ltd.) for 5 minutes, to which 150 ml of pure water was added, and the mixture was kneaded for 10 minutes.

The kneaded mixture was dried at 40° C. under reduced pressure, the dried material was pulverized by an atomizer to give a composite (50 weight %). The composite was white powders.

COMPARATIVE EXAMPLE 1

500 g of calcium pantothenate and 500 g of calcium carbonate were sieved through a 60-mesh sieve and mixed in a mixer.

TEST EXAMPLE 1

Two g of one of the calcium pantothenate composites obtained in the Examples 1 to 4 and in the Comparative Example 1 and 10 g of ascorbic acid were placed in a glass bottle and stored at 50° C. and at 68% of RH (relative humidity) for two weeks without stopper. After the two weeks the calcium pantothenate composites and the powders mixed with ascorbic acid were analyzed for the loss on drying and the content of calcium pantothenate.

The results are summarized in Table 1.

TABLE 1

|  | before storage | | after 2-weeks storage at 50° C. and RH 68% | |
| --- | --- | --- | --- | --- |
|  | loss on drying | content of calcium pantothenate | loss on drying | content of calcium pantothenate |
| E.1 | 0.4% | 97.2% | 0.86% | 84.5% |
| E.2 | 0.2% | 100.2% | 2.1% | 81.7% |
| E.3 | 0.2% | 99.6% | 2.3% | 78.7% |
| E.4 | 0.2% | 101.1% | 2.2% | 78.9% |
| C.E.1 | 0.1% | 103.0% | 3.9% | 53.2% |
| C.E.2 | 0.1% | 100.0% | 3.7% | 39.8% |

Note) Comparative Example 2
A mixture of 10 g of ascorbic acid and 1 g of calcium pantothenate (JP grade) was tested

EXAMPLE 5

50 g of calcium pantothenate (Daiichi Seiyaku Co., Ltd.: JP grade) and 150 g of calcium lactate were mixed in a mortar, to which 20 ml of pure water was added, and the mixture was kneaded. The kneaded mixture was dried at 40° C. under reduced pressure, the dried material was pulverized by a table grinder to give a composite (containing 25 weight % of calcium pantothenate). The composite was white powders.

EXAMPLE 6

100 g of calcium pantothenate (Daiichi Seiyaku Co., Ltd.: JP grade) and 100 g of calcium lactate were mixed in a mortar, to which 20 ml of pure water was added, and the mixture was kneaded. The kneaded mixture was dried at 40° C. under reduced pressure, the dried material was pulverized by a table grinder to give a composite (50 weight %). The composite was white powders.

EXAMPLE 7

150 g of calcium pantothenate (Daiichi Seiyaku Co., Ltd.: JP grade) and 50 g of calcium lactate were mixed in mortar, to which 20 ml of pure water was added, and the mixture was kneaded. The kneaded mixture was dried at 40° C. under reduced pressure, the dried material was pulverized by a table grinder to give a composite (75 weight %). The composite was white powders.

EXAMPLE 8

50 g of calcium pantothenate (Daiichi Seiyaku Co., Ltd.: JP grade) and 150 g of magnesium carbonate were mixed in a mortar, to which 20 ml of pure water was added, and the mixture was kneaded. The kneaded mixture was dried at 40° C. under reduced pressure, the dried material was pulverized by a table grinder to give a composite (25 weight %). The composite was white powders.

EXAMPLE 9

100 g of calcium pantothenate (Daiichi Seiyaku Co., Ltd. JP grade) and 100 g of magnesium carbonate were mixed in a mortar, to which 20 ml of pure water was added, and the mixture was kneaded. The kneaded mixture was dried at 40° C. under reduced pressure, the dried material was pulverized by a table grinder to give a composite (50 weight %). The composite was white powders.

EXAMPLE 10

50 g of calcium pantothenate (Daiichi Seiyaku Co., Ltd.: JP grade) and 150 g of magnesium carbonate were mixed in a mortar, to which 20 ml of pure water was added, and the mixture was kneaded. The kneaded mixture was dried at 40° C. under reduced pressure, the dried material was pulverized by a table grinder to give a composite (75 weight %). The composite was white powders.

EXAMPLE 11

50 g of calcium pantothenate (Daiichi Seiyaku Co., Ltd.: JP grade) was dissolved in 500 ml of pure water, to which 50 g of calcium lactate was added to give a dispersion. The dispersion was subjected to spray drying under the following conditions to give a composite (50 weight %). (Conditions of spray drying: apparatus; NIRO, ATOMIZER, spray type: disc, spray pressure: 2.5 kg/cm$^2$, spray liquid quantity: 23 ml/min., aeration temperature: 135° C., exhaust gas temperature: 70° C.).

EXAMPLE 12

50 g of calcium pantothenate (Daiichi Seiyaku Co., Ltd.; JP grade) was dissolved by warming at 80° C. in 50 ml of pure water. 50 g of calcium lactate was dissolved by warming at 80° C. in 100 ml of pure water, to which all of the calcium pantothenate solution described above was added with stirring, and the mixed solution was allowed to stand at room temperature for 2 hours. Crystals were deposited with a decrease in temperature and elapse of time. After 2 hours, all of the mixture became a creamy solid.

The creamy solid was dried at 40° C. under reduced pressure, the dried material was pulverized by a table grinder to give a composite (containing 50 weight % of calcium pantothenate). The composite was white powders.

EXAMPLE 13

50 g of calcium pantothenate (Daiichi Seiyaku Co., Ltd.; JP grade) and 50 g of calcium lactate were dissolved by warming at 80° C. in 150 ml of pure water, and the mixed solution was allowed to stand at room temperature for 2 hours. Crystals were deposited with a decrease in temperature and elapse of time. After 2 hours, all of the mixture became a creamy solid.

The creamy solid was dried at 40° C. under reduced pressure, the dried material was pulverized by a table grinder to give a composite (50 weight %). The composite was white powders.

EXAMPLE 14

50 g of calcium pantothenate (Daiichi Seiyaku Co., Ltd.; JP grade) and 50 g of calcium lactate were mixed in a mortar, to which 50 ml of pure water-ethyl alcohol mixture (1:1) was added, and the mixture was kneaded. The kneaded mixture was dried at 40° C. under reduced pressure, the dried material was pulverized by a table grinder to give a composite (50 weight %). The composite was white powders.

EXAMPLE 15

50 g of calcium pantothenate (Daiichi Seiyaku Co., Ltd.; JP grade) and 50 g of calcium lactate were mixed in a mortar, to which 125 ml of methyl alcohol was added, and the mixture was kneaded. The kneaded mixture was dried at 40° C. under reduced pressure, the dried material was pulverized by a table grinder to give a composite (50 weight %). The composite was white powders.

EXAMPLE 16

50 g of calcium pantothenate (Daiichi Seiyaku Co., Ltd.; JP grade) and 50 g of calcium lactate were added to 400 ml of pure water-ethyl alcohol mixture (1:1) to give a dispersion. The dispersion was subjected to spray drying under the following conditions to give a composite (50 weight %). (Conditions of spray drying: apparatus; NIRO, ATOMIZER, spray type: disc, spray pressure: 2.5 kg/cm$^2$, spray liquid quantity: 23 ml/min., aeration temperature: 105° C., exhaust gas temperature: 60° C.).

EXAMPLE 17

50 g of calcium pantothenate (Daiichi Seiyaku Co., Ltd.; JP grade) and 50 g of calcium lactate were added to 200 ml of ethyl alcohol to give a dispersion. The dispersion was subjected to spray drying under the following conditions to give a composite (50 weight %). (Conditions of spray drying: apparatus; NIRO, ATOMIZER, spray type: disc, spray pressure: 2.5 kg/cm$^2$, spray liquid quantity: 23 ml/min., aeration temperature: 105° C., exhaust gas temperature: 60° C.).

TEST EXAMPLE 2

An amount of each composite obtained in the Examples 5 to 11 and 14 to 17, equivalent to 1 g of calcium pantothenate, was mixed thoroughly with 10 g of ascorbic acid, placed into a glass bottle, and stored at 50° C. and RH68% for two weeks without stopper. After the two weeks the mixture was analyzed for the loss on drying and the content of calcium pantothenate.

The results are summarized in Table 2.

TABLE 2

Results of the accelerated stability test of mixtures of calcium pantothenate composite and ascorbic acid
The content values in the Table mean the remaining percentages.

| | before storage | after 2-weeks storage at 50° C. and RH 68% | | | |
|---|---|---|---|---|---|
| | loss on drying (%) | loss on drying (%) | content of calcium pantothenate | content of ascorbic acid | note |
| E.5 | 4.9 | 5.1 | 100.3% | 98.8% | calcium 75% |
| E.6 | 1.6 | 1.7 | 100.4 | 99.5 | lactate 50 |
| E.7 | 0.8 | 2.2 | 93.2 | 99.5 | 25 |
| E.8 | 0.6 | 16.7 | 101.7 | 100.7 | magnesium 75% |
| E.9 | 0.3 | 9.5 | 88.9 | 101.8 | carbonate 50 |
| E.10 | 0.3 | 5.2 | 78.5 | 97.1 | 25 |
| E.11 | 1.0 | 2.3 | 94.2 | 94.1 | calcium 50% |
| E.14 | 1.0 | 1.7 | 95.4 | 99.8 | lactate |
| E.15 | 0.8 | 1.6 | 104.0 | 96.1 | |
| E.16 | 2.0 | 1.7 | 97.9 | 97.3 | |

TABLE 2-continued

Results of the accelerated stability test of mixtures of calcium pantothenate composite and ascorbic acid
The content values in the Table mean the remaining percentages.

| | before storage | after 2-weeks storage at 50° C. and RH 68% | | | |
|---|---|---|---|---|---|
| | loss on drying (%) | loss on drying (%) | content of calcium pantothenate | content of ascorbic acid | note |
| E.17 | 1.0 | 2.6 | 97.2 | 95.6 | |
| C.E.5 | 0.1 | 3.7 | 39.8 | 95.9 | none |

Note) Comparative Example 3
A mixture of 10 g of ascorbic acid and 1 g of calcium pantothenate (JP grade) was tested.

APPLICATION EXAMPLE

Vitamin complex tablets were prepared by using the calcium pantothenate composite obtained in the Example 3, and the stability of each vitamin was examined. The formula is shown in Table 3. The tablets were prepared by direct compression, and coated with water-soluble film.

TABLE 3

Formula for mineral-enriched vitamin complex tablets

| ingredient | theoretical amount in 2 tablets | actual amount in 2 tablets |
|---|---|---|
| vitamin A palmitate | 5000 I.U. | 16.7 mg |
| vitamin D$_3$ | 400 I.U. | 4.0 mg |
| vitamin E | 30 I.U. | 60.0 mg |
| vitamin C | 600 mg | 649.5 mg |
| vitamin B$_1$ | 15 mg | 16.2 mg |
| vitamin B$_2$ | 15 mg | 15.0 mg |
| nicotinamide | 100 mg | 100.0 mg |
| vitamin B$_6$ | 5 mg | 5.3 mg |
| vitamin B$_{12}$ | 12 mg | 13.2 mg |
| calcium pantothenate | 20 mg | 44.0 mg |
| folic acid | 0.4 mg | 0.44 mg |
| iron | 18 mg | 54.8 mg |
| copper | 2 mg | 2.3 mg |
| zinc | 15 mg | 18.7 mg |
| crystalline cellulose | | 119.86 mg |
| anhydrous silicic acid | | 12.0 mg |
| calcium carboxymethylcellulose | | 60.0 mg |
| magnesium stearate | | 8.0 mg |
| total in 2 tablets | | 1200.0 mg |

COMPARATIVE APPLICATION EXAMPLE

In the formula for the Application Example, 22 mg of the JP calcium pantothenate powders in 2 tablets was used in place of 44 mg of the calcium pantothenate composite (50% powders) in 2 tablets. The shortage was covered by addition of anhydrous monobasic calcium phosphate. The method of preparation was in accordance with that in the Application Example.

TEST EXAMPLE 3

100 tablets each of the preparations obtained in the Application Example and in the Comparative Application Example were put into glass bottles and stored at 50° C. and RH 68%. After 2 and 4 weeks, the tablets were analyzed for the loss on drying and the content of each vitamin.

Among the results, the loss on drying and the content of calcium pantothenate and of vitamin B$_1$ are listed in Table 4.

TABLE 4

| storage condition | item of analysis | Application Example | Comparative Application Example |
|---|---|---|---|
| before storage | loss on drying | 2.1% | 1.6% |
| | content of calcium pantothenate | 110.3% | 109.6% |
| | content of vitamin $B_1$ | 107.0% | 106.5% |
| after 2-weeks storage at 50° C. RH 68% | loss on drying | 3.7% | 3.8% |
| | content of calcium pantothenate | 106.3% | 91.2% |
| | content of vitamin $B_1$ | 96.7% | 95.5% |
| after 4-weeks storage at 50° C. RH 68% | loss on drying | 5.1% | 4.6% |
| | content of calcium pantothenate | 96.6% | 63.2% |
| | content of vitamin $B_1$ | 88.4% | 84.2% |

The results described above show that calcium pantothenate may be stabilized by a very simple technique when the calcium pantothenate composites in this invention are used for preparation of vitamin complex tablets.

What is claimed is:

1. A composite which is obtained by mixing calcium pantothenate with a salt selected from the group consisting of calcium lactate, magnesium carbonate and calcium carbonate in the presence of water and/or lower alcohol, and drying the resulting mixture, the amount of the said salt employed being sufficient to constitute 40 to 75 weight % of the total amount of the composite, and the amount of water and/or lower alcohol employed being 10 to 200 volume parts per 100 weight parts of the mixture of calcium pantothenate and the said salt.

2. A composite as claimed in claim 1, wherein the lower alcohol is methyl alcohol or ethyl alcohol.

3. A composite as claimed in claim 1, said composite is in the form of granules or powder.

4. A composite as claimed in claim 1, wherein the salt is calcium lactate or carbonate.

5. A composite as claimed in claim 1, wherein the salt is calcium lactate.

6. A composite as claimed in claim 5, said composite is in the form of granules or powder.

7. A composite as claimed in claim 5, said composite being obtained by dissolving calcium pantothenate and calcium lactate into water and/or a lower alcohol, and allowing the solution to stand to give crystals, and drying the resulting crystals.

8. A process for producing a composite which comprises mixing calcium pantothenate with a salt selected from the group consisting of calcium lactate, magnesium carbonate and calcium carbonate in the presence of water and/or a lower alcohol, and drying the resulting mixture, the amount of said salt employed being sufficient to constitute 40 to 75 weight % of the total amount of the composite, and the amount of water and/or lower alcohol employed being 10 to 200 volume parts per 100 weight parts of the mixture of calcium pantothenate and the said salt.

* * * * *